United States Patent [19]
Luukkala

[11] Patent Number: 5,467,944
[45] Date of Patent: Nov. 21, 1995

[54] DETECTOR FOR INDICATING ICE FORMATION ON THE WING OF AN AIRCRAFT

[75] Inventor: Mauri Luukkala, Espoo, Finland

[73] Assignee: Soundek Oy, Finland

[21] Appl. No.: 116,880

[22] Filed: Sep. 7, 1993

[30] Foreign Application Priority Data

Sep. 8, 1992 [FI] Finland ................... 924007

[51] Int. Cl.⁶ ..................... B64D 15/22
[52] U.S. Cl. ............. 244/134 F; 340/582; 73/599
[58] Field of Search .......... 244/134 R, 134 D, 244/134 F; 340/582, 581; 73/599

[56] References Cited

U.S. PATENT DOCUMENTS

| | | | |
|---|---|---|---|
| 2,419,454 | 4/1947 | Le Clair. | |
| 3,412,326 | 11/1968 | Jones et al. | 340/581 |
| 3,541,540 | 11/1970 | Hughes | 340/582 |
| 4,054,255 | 10/1977 | Magenheim | 244/134 F |
| 4,335,613 | 6/1982 | Luukkala | 340/582 |
| 4,461,178 | 7/1984 | Chamuel | 244/134 F |
| 4,604,612 | 8/1986 | Watkins et al. | 244/134 F |

FOREIGN PATENT DOCUMENTS

| | | | |
|---|---|---|---|
| 0267823 | 5/1988 | European Pat. Off. | 244/134 F |
| 0100621 | 7/1988 | European Pat. Off. | |
| 2640349 | 3/1978 | Germany | 244/134 F |

*Primary Examiner*—Galen L. Barefoot
*Attorney, Agent, or Firm*—Vickers, Daniels & Young

[57] ABSTRACT

A detector indicating ice formation on the wing of an aircraft or any planear surface, based on a thread-like or a tape-like transducer, through which an ultrasonic signal is transmitted at one end. The attenuation of the signal having passed through the thread is measured with a receiver at the opposite end while the thread is simultaneously being heated such that ice that may surround it melts again, the attenuation thus resuming its initial level.

38 Claims, 1 Drawing Sheet

DETECTOR FOR INDICATING ICE FORMATION ON THE WING OF AN AIRCRAFT

The present invention pertains to an improved ice detector and more particularly to an improved ice detector for detecting ice formation on aircraft wings.

THE BACKGROUND OF THE INVENTION

In modern aircrafts the wing profile is crucial for the flight. If this profile is altered for some reason, the flying characteristics and consequently the stalling characteristics of the wing are significantly deteriorated.

The wing profile hardly changes in normal conditions, except when ice is formed on the wing surface for various reasons. In fact, ice formation on the wings of aircrafts has become a noticeable hazard in air traffic, since it has been noted that the ice layers may grow a thickness of up to one inch, whereby the flying characteristics of the wing are substantially weakened. Ice formation on the wing has proved to be the very reason for a number of recent passenger flight accidents. Ice formation involves a second drawback: in many jet planes the motors and their air intakes are located at the rear end of the fuselage, implying that, as the wing is bent at takeoff, ice is detached and absorbed directly into the air intakes of the motor, causing the turbine wings of the motor to break.

Ice formation may occur in various ways: during the flight weather conditions may be such that ice starts forming on the wings; also weather conditions during taxiing may generate ice on the surface of the wing; however, the most unexpected situation arises, when an aircraft having flown at high altitudes at a low temperature (e.g. −50° C.) accumulates a thick ice layer on its wings after landing at the airport. This is due to the fact that the fuel has been deeply cooled in its tank during the flight. The design of fuel tanks allow the fuel to get into contact with the upper surface of the wing, the upper surface of the wing being extremely cooled and accumulating ice on the surface, although the air temperature at the airport would be above zero. This ice formation process has been difficult to verify and has caused surprises in air traffic. Aircraft manufacturers have of course taken measures to eliminate the risks caused by ice formation. The most common method is spraying the wings with glycol liquid, which melts snow and ice that may have accumulated on the wing. Another method consists in checking the humidity and the temperature of outside air, enabling to anticipate conditions in which ice formation occurs, and to conduct combustion heat from the motors to the front edge of the wing to melt the ice. A special ice detector is further provided at the front end of the fuselage, an ice formation alarm going off if ice is formed on the surface of the detector. In this situation, precautions can be taken to prevent ice formation. Nevertheless, this detector does not indicate whether ice has accumulated precisely on the surface of the wing.

Finnair in particular has implemented a very simple ice detection in their aircraft: a special kind of strips are fixed on the surface of the wing, the strips fluttering in the air current if the wing surface is bare and no ice is present. Furthermore, Finnair has used a kind of clearly visible flange that can be observed from the ground. If the flange and the scale attached to it cannot be clearly seen, this implies that there is ice on the wing surface.

As to prior art, we note that the most common solution is a detector attached to the front end of the fuselage, the detector consisting of a short, vibrating stick which vibrates continuously at its natural resonance frequency. If ice is formed on the vibrator stick, the ice and its high viscosity will change the vibration frequency and attenuate the vibration amplitude. A slightly different detector based on ultrasonics placed at any point on the wing, has been recently launched. This detector consists of a metal disc mounted on the surface of the wing plane, and an ultrasonic crystal below the disc causes the metal disc to vibrate. If water is present on the disc, the viscosity of water is low enough not to attenuate the vibration. Conversely, if the water on the disc freezes, the viscosity is altered abruptly, and the vibration amplitude decreases noticeably, the decrease being detectable at the ultrasonic crystal under the disc. This detector has the advantage of being mountable at the point of the fuel tank, whereby it detects the ice formation at the very point where this would be hazardous. The drawback of this detector is difficult mounting, since it must be mounted inside the fuel tank, which is a dangerous and expensive solution because of explosion risks, among others. In addition, this detector detects ice formation only at a given, spot-like point, which is not sufficient for total security.

FI patent specification 61249 describes an ultrasonic detector enabling to detect the presence of "black ice" on a bituminous road by transmitting an ultrasonic pulse along a thin thread, the pulse being subsequently reflected at the end of the thread. If the thread is covered with ice, no echo pulse will be obtained at the end of the thread. This detector has the inconvenience that partial freezing of the thread or the thread holders pressing the thread to the support surface may cause an extra reflection or false echo which reduces the operating reliablity of the detector. Moreover, the detection electronics required for the detector is relatively complicated. It is known that aviation electronics must be as reliable and straightforward as possible.

SUMMARY OF THE INVENTION

The present invention is mainly characterized by the feature that the device comprises as a measuring transducer, a thin thread-like or tape-like acoustic waveguide having an ultrasonic transmitter at one end and an ultrasonic receiver at the other end, and that the device comprises electronic devices for measuring the intensity and the attenuation of an ultrasonic pulse having passed through the transducer thread in the case of ice formation, and that the electric resistance of the thread is measured simultaneously with the measurement of the attenuation of the ultrasound, and that the thread can be optionally heated electrically to melt surrounding ice, whereby the ultrasound intensity resumes its initial level.

The ice formation detector according to the invention is based on the feature that a mechanical ultrasonic signal is transmitted along a thin thread or strip at one end, and the intensity of the ultrasonic signal having passed through the thread is measured at the other end. If the thread is covered with a water layer, the ultrasound will not be attenuated, however if the water freezes, the ultrasound cannot propagate in the thread, but will be abruptly attenuated. If the thread is covered with sludge, the ultrasound will be somewhat attenuated to a kind of intermediate level, at which detection of sludge is also possible. There is a great viscosity difference between ice and water, and thus the intensity of the ultrasound having passed through the thread will also be highly different. The thread being used may have a diameter of 1 to 2 mm and it can be replaced by a tape-like waveguide. The thread may be made of say steel, nickel or any other material having a similar low acoustic attenuation, magnetostrictive nickel being however the most appropriate, since it is not corrosive, it has a relatively high electric resistance (for electric heating) and an ultrasound can easily be generated in it by means of a magnetostrictive transducer (or piezoelectric transducer). It is known per se that an ultrasound can be generated in a thin thread by magnetostriction by winding a coil around the thread, and an ultrasonic pulse being generated also in the thread by conducting an electric pulse to the coil. An ultrasonic pulse can be received with a similar coil and transformed into an electric signal. An essential feature of this invention is that it is not based on the "pulse-echo" principle, but on the ultrasonic signal having passed through the thread and on the detection of its attenuation. If no ice occurs on the thread the signal having passed through will be unattenuated and the situation is under control. Only when the signal having passed through is abruptly attenuated, it is probable that ice has been formed on the thread. The transducer thread itself is mounted on the wing as described below. Another essential advantage is that the receiver does not have to be synchronized with the transmission pulse, which simplifies the electronics considerably, and the receiver may be switched on all the time. The reason for the disappearance of the ultrasonic pulse having passed through may also be that the thread is broken. However, breakage of the thread is easily detected by measuring the resistance of the thread from one end to the other at the point of the detectors. If the resistance is unaltered, the attenuation is not due to breakage of the thread. When the thread is being mounted on the wing of an aircraft, the mounting is carried out on an insulated support in order to avoid short-circuiting of the thread resistance by the metal wing. A supplementary checking is done by heating the thread with electric current via resistance measuring contacts so that ice around the thread melts again. Now the supersonic signal, which has already been attenuated once, should return, since the thread is only surrounded by water. By these means the necessary safety is provided for the ice indicator according to the invention.

The primary object of the present invention is the provision of a device which accurately detects ice formation by use of ultrasound.

Another object of the present invention is a device to detect ice on an aircraft.

Still another object of the present invention is an ice detector having a simple yet reliable design and operation for ice detection on aircrafts.

These and other objects and advantages of the invention will become, apparent from the detailed description of the invention taken in conjunction with the drawings.

DESCRIPTION OF THE PREFERRED EMBODIMENT

Figure 1:
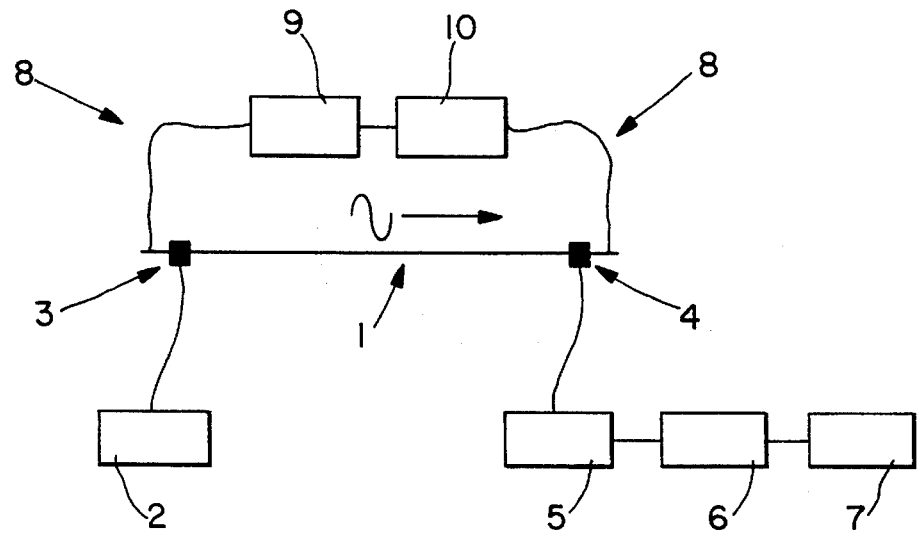
FIG. 1 shows the device according to the invention as a block diagram.

Referring now to the drawings, wherein the showings are for the purpose of illustrating the preferred embodiment of the invention only and not for the purposes of limiting the same, reference is first made to FIG. 1 which illustrates ultrasonics.

Pulses at an appropriate frequency, preferably in the range of 150 to 250 kHz, are generated in the transducer thread 1 by an electronically pulsated signal generator 2. This ultrasonic signal is generated in the ultrasonic transducer 3 at the end of the thread, which has been attached to the transducer thread such that the ultrasound is transferred to the transducer thread in a suitable manner. The transducer 3 may be for instance a piezoceramic transducer having an appropriate opening into which the thread is threaded, or else the transducer may be a magnetostrictive transducer known as such, consisting of a coil wound around the thread. An identical transducer 4 is provided at the other end of the transducer thread 1 to receive a transmitted ultrasonic signal and to transform it into an electronic signal which is detectable with an electronic amplifier 5, which amplifies the received signal to such an intensity that it can be treated by means known per se in electronics, for instance by taking the received signal to a threshold detector 6, which gives an alarm with the alarm device 7 if the level of the ultrasonic signal having passed through the transducer thread has been too much reduced. The device according to the invention comprises further as an essential part measuring conductors 8 attached to each end of the transducer thread, by means of which the resistance of the thread and its variations can be continuously measured with an electronic meter 9. The same conductors may optionally be used for heating the transducer thread with the heater 10 so as to melt the ice possibly surrounding the thread 1, which provides an additional confirmation of potential ice formation. Thus the operation of the device according to the invention is such that in a normal situation, when the transducer thread is not surrounded by ice, or when it is surrounded by water or perhaps a liquid anti-freeze agent, such as glycol, the ultrasound transmitted along the transducer thread is not attenuated and the receiver 5 detects an intense supersonic signal and the threshold detector 6 connected to the receiver 5 does not give any alarm. If the transducer thread is covered with ice the ultrasound is abruptly attenuated and the receiver 5 and the threshold detector 6 do not detect any signal, whereby the pilot's cockpit receives a freezing alarm. Breakage of the thread is detected by continuously measuring the resistance of the thread, which increases strongly when the thread is broken, as is known. When a freezing alarm goes off, vital extra confirmation is obtained by heating the thread electrically until the surrounding ice melts. At this moment the freezing alarm should stop.

Figure 2:
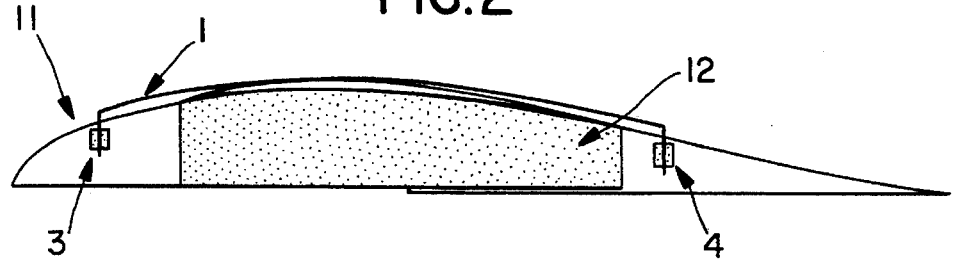
FIG. 2 is a schematic view of the placement of the transducer on the wing of an aircraft.
Figure 3:
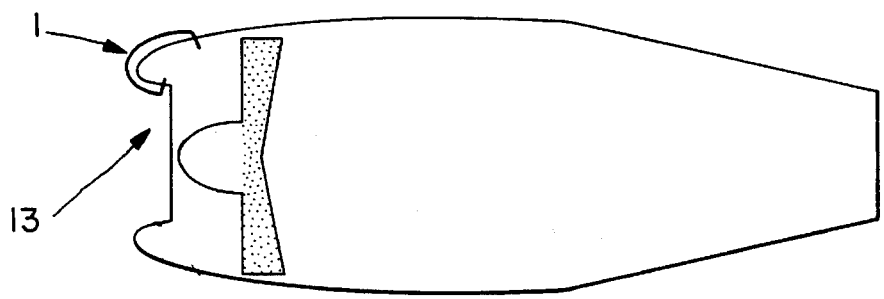
FIG. 3 is a schematic view of the placement of the transducer at the mouth of an air intake of the motor.
Figure 4:
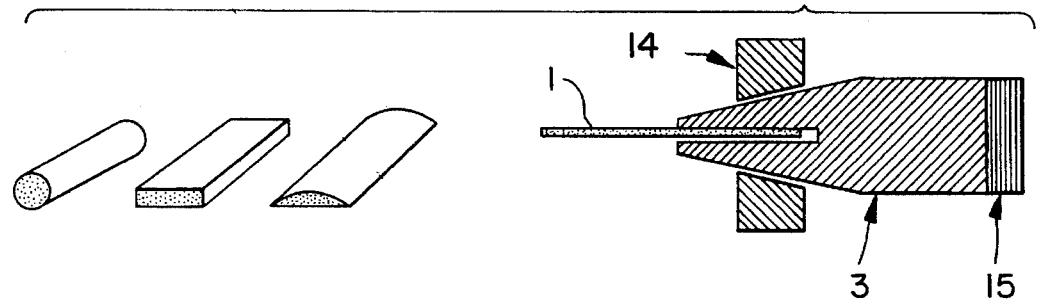
FIG. 4 is a schematic view of some optional cross-sections of the transducer thread as well as a removable spindle-type transducer.

FIG. 2 shows the mounting of the transducer thread on the wing 11 of an aircraft above the fuel tank 12. The thread can be bent through holes in the wing so that the transducers and their electric contacts will be located below the surface of the wing. It is obvious that the thread should be mounted in the direction of the air current so as to create a minimum of turbulence. FIG. 3 illustrates an optional mounting of the transducer thread in the air intake 13 of a jet motor. FIG. 4 illustrates the various optional cross-sections of the transducer thread 1. A round transducer thread may have a diameter of 1 to 2 mm, which does not disturb the aerodynamics of the wing. A transducer which actually is a waveguide may also have the shape of a strap or a semi-circle. It is easier to attach such transducers to the wing surface than round ones. An insulating layer, e.g. epoxy paint, should be applied to the wing surface below the transducer thread, allowing to measure the resistance without problems. The device according to the invention can also be used to detect various intermediate freezing stages, such as the presence of sludge or the presence of thick anti-freeze glycol, by checking the amplitude of the ultrasound passing through in various intermediate situations, The device according to the invention enables to measure ice formation on a very large area, e.g. over the entire fuel tank, and if necessary, several transducer threads can be mounted along the wing.

In the device according to the present invention echo signals are not detected, but an ultrasonic signal having passed through the thread, which is not sensitive to false echoes. Further this device is not sensitive to the length of the thread since the standing waves of ultrasound are not being used, but specifically pulse-like propagating waves. The ultrasonic transducer 3 at the end of the transducer thread may also consist of a kind of a spindle tightened and loosened with a nut 14, in the way a bit is attached to the spindle in drilling machines. The actual piezocrystal 15 is located at one end of the spindle, from where the ultrasound can proceed via the spindle jaws to the transducer thread 1 as in FIG. 4. In this way the supersonic transducer is easily detached and attached anew.

Modifications and alterations will occur to others upon the reading and understanding of the specification. It is intended that such modifications and alterations be included insofar as they come within the scope of the claims with equivalents thereof.

Having defined the invention, the following is claimed:

1. A device which uses ultrasonic transmissions to detect ice formation on a material comprising an acoustic waveguide electrically insulated from said material having a first end and a second end, ultrasonic transmitter means for sending at least one ultrasonic pulse through said first end of said acoustic waveguide, ultrasonic receiver means for measuring the intensity of said ultrasonic pulse at the second end of said ultrasonic waveguide and means for detecting damage to said waveguide, said intensity of said ultrasonic pulse being reduced by ice formation on said acoustic waveguide.

2. A device as defined in claim 1, wherein said means for detecting damage to said waveguide includes means for detecting electrical resistance through said acoustic waveguide.

3. A device as defined in claim 2, including means for electrically heating said acoustic waveguide.

4. A device as defined in claim 3, wherein said acoustic waveguide includes a metal selected from the group consisting of steel, nickel, magnetostrictive nickel and other low acoustic attenuation metals.

5. A device as defined in claim 4, wherein said metallic acoustic waveguide is selected from the group consisting of steel, nickel, magnetostrictive nickel and other low acoustic attenuation metals.

6. A device as defined in claim 5, wherein said ultrasonic transmitter is selected from the group consisting of a piezoceramic transducer and a magnetostrictive transducer.

7. A device as defined in claim 6, wherein said ultrasonic transmitter generates a 150–250 kHz ultrasonic pulse.

8. A device as defined in claim 7, including an alarm which activates when said measured ultrasonic pulse is attenuated.

9. A device as defined in claim 1, including means for electrically heating said acoustic waveguide.

10. A device as defined in claim 1, wherein said acoustic waveguide is a metallic thread having a diameter of 1–2 mm.

11. A device as defined in claim 10, wherein said metallic acoustic waveguide is selected from the group consisting of steel, nickel, magnetostrictive nickel and other low acoustic attenuation metals.

12. A device as defined in claim 11, wherein said ultrasonic transmitter is selected from the group consisting of a piezoceramic transducer and a magnetostrictive transducer.

13. A device as defined in claim 1, wherein said acoustic waveguide is a metallic tape.

14. A device as defined in claim 13, wherein said metallic acoustic waveguide is selected from the group consisting of steel, nickel, magnetostrictive nickel and other low acoustic attenuation metals.

15. A device as defined in claim 14, wherein said ultrasonic transmitter is selected from the group consisting of a piezoceramic transducer and a magnetostrictive transducer.

16. A device as defined in claim 1, wherein said acoustic waveguide includes a metal selected from the group consisting of steel, nickel, magnetostrictive nickel and other low acoustic attenuation metals.

17. A device as defined in claim 1, wherein said ultrasonic transmitter is selected from the group consisting of a piezoceramic transducer and a magnetostrictive transducer.

18. A device as defined in claim 1, wherein said ultrasonic transmitter generates a 150–250 kHz ultrasonic pulse.

19. A device as defined in claim 1, including an alarm which activates when said measured ultrasonic pulse is attenuated.

20. A device as defined in claim 1, wherein said material is a wing of an aircraft.

21. A device which uses ultrasonic transmissions to detect ice formation on an aircraft by measuring the effect of ice on the strength of said ultrasonic transmissions comprising an acoustic waveguide positioned on the wing of said aircraft and electrically insulated from said wing, ultrasonic transmitter means for sending an ultrasonic signal through said acoustic waveguide and to ultrasonic receiver means, said ultrasonic receiver means detects the intensity of said ultrasonic signal, means for measuring electrically resistance in said waveguide and means for electrically heating said waveguide when ice forms on said waveguide.

22. A device as defined in claim 21, including alarm means for indicating reduced intensity of said ultrasonic signal, said alarm means activating when said ultrasonic signal intensity falls below a predetermined level and said means for electrically heating said waveguide activates when said alarm means activates.

23. A device as defined in claim 21, wherein said waveguide is metallic and has a cross-sectional shape selected from the group consisting of circular, semi-circular and rectangular.

24. A device as defined in claim 21, wherein said ultrasonic transmitter means includes spindle jaws and a spindle jaw nut to attach and detach said waveguide from said ultrasonic transmitter and said ultrasonic transmitter means includes a piezocrystal located adjacent to said spindle jaws.

25. A device as defined in claim 23, wherein said ultrasonic transmitter means includes spindle jaws and a spindle jaw nut to attach and detach said waveguide from said ultrasonic transmitter and said ultrasonic transmitter means includes a piezocrystal located adjacent to said spindle jaws.

26. A device as in claim 22, wherein said alarm and said electrical heating means are deactivated when said ultrasonic receiver means detects an unattenuated ultrasonic signal.

27. A device as in claim 21, wherein said insulating layer is epoxy paint.

28. A device as defined in claim 21, wherein said acoustic waveguide is selected from the group consisting of steel, nickel, magnetostrictive nickel and other low acoustic attenuation metals.

29. A method for detecting ice formation on an aircraft comprising:
   (a) placing an acoustic waveguide on the aircraft, said waveguide having a first end and a second end and electrically insulated from said aircraft;
   (b) connecting ultrasonic transmitter means to said first end of said waveguide, said transmitter means capable of sending at least one ultrasonic pulse through said waveguide, the intensity of said ultrasonic pulse being reduced by ice formation on said waveguide;
   (c) connecting ultrasonic receiver means to said second end of said waveguide, said receiver means capable of detecting said intensity of said at least one ultrasonic pulse;
   (d) connecting waveguide damage detection means to said first end and said second end of said waveguide for detecting electrical resistance through said waveguide; and
   (e) activating icing alarm when said receiver means detects said at least one ultrasonic pulse having an intensity which is lower than said intensity of said at least one ultrasonic pulse sent by said transmitter means.

30. A method according to claim 29, including the step of connecting heating means to said waveguide, said heating means controlling the electrical current level in said waveguide.

31. A method according to claim 30, including the step of signaling said heating means to increase said current level in said waveguide to heat said waveguide and melt the ice which has formed on said waveguide when said icing alarm activates.

32. A method according to claim 29, including the step of deactivating said ice alarm when said intensity of said ultrasonic pulse detected by said receiver means is similar to said ultrasonic pulse intensity produced by said transmitter means.

33. A method according to claim 31, including the step of deactivating said ice alarm when said intensity of said ultrasonic pulse detected by said receiver means is similar to said ultrasonic pulse intensity produced by said transmitter means.

34. A method according to claim 33, including the step of signaling said heating means to reduce said current level in said waveguide when said ice alarm is deactivated.

35. A method according to claim 32, including the step of measuring the time intervals between said ice alarm activation and ice alarm deactivation for determining the rate of said ice formation on said aircraft.

36. A method according to claim 34, including the step of measuring the time intervals between said ice alarm activation and ice alarm deactivation for determining the rate of said ice formation on said aircraft.

37. A method according to claim 29, including the step of activating a waveguide damage alarm when said waveguide damage detection means detects a high electrical resistance through said waveguide.

38. A method according to claim 36, including the step of activating a waveguide damage alarm when said waveguide damage detection means detects a high electrical resistance through said waveguide.

* * * * *